US008951296B2

(12) United States Patent
Melder et al.

(10) Patent No.: US 8,951,296 B2
(45) Date of Patent: Feb. 10, 2015

(54) DEVICES AND METHODS FOR PHOTODYNAMICALLY MODULATING NEURAL FUNCTION IN A HUMAN

(71) Applicant: Medtronic Ardian Luxembourg S.a.r.l., Luxembourg (LU)

(72) Inventors: Robert J. Melder, Santa Rosa, CA (US); Ayala Hezi-Yamit, Windsor, CA (US); Christopher W. Storment, Sonoma, CA (US); Carol M. Sullivan, Petaluma, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 9 days.

(21) Appl. No.: 13/826,604

(22) Filed: Mar. 14, 2013

(65) Prior Publication Data
US 2014/0005591 A1 Jan. 2, 2014

Related U.S. Application Data

(60) Provisional application No. 61/666,687, filed on Jun. 29, 2012.

(51) Int. Cl.
*A61N 5/00* (2006.01)
*A61N 5/06* (2006.01)
(Continued)

(52) U.S. Cl.
CPC ............ *A61N 5/062* (2013.01); *A61N 5/0601* (2013.01); *A61N 2005/063* (2013.01);
(Continued)

(58) Field of Classification Search
None
See application file for complete search history.

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

WO WO-9525472 9/1995
WO WO-9736548 10/1997
(Continued)

OTHER PUBLICATIONS

Shea et al., Mechanistic Investigation of Doxycycline Photosensitization by Picosecond-pulsed and Continuous Wave Laser Irradiation of Cells in Culture, The Journal of Biological Chemistry, vol. 265, No. 11, Issue of Apr. 15, pp. 5977-5982, 1990.*

(Continued)

*Primary Examiner* — Lynsey Crandall
*Assistant Examiner* — Manolis Pahakis

(57) ABSTRACT

Devices and methods for therapeutic photodynamic modulation of neural function in a human. One embodiment of a method in accordance with the technology includes administering a photosensitizer to a human, wherein the photosensitizer preferentially accumulates at nerves proximate a blood vessel compared to non-neural tissue of the blood vessel. The method can further include irradiating the photosensitizer using a radiation emitter positioned within the human, wherein the radiation has a wavelength that causes the photosensitizer to react and alter at least a portion of the nerves thereby providing a therapeutic reduction in sympathetic neural activity. Several embodiments of the technology are useful for disrupting renal nerves, such as renal denervation, for treating hypertension, diabetes, congestive heart failure, and other indications.

24 Claims, 11 Drawing Sheets

(51) Int. Cl.
*A61N 5/067* (2006.01)
*A61B 18/00* (2006.01)

(52) U.S. Cl.
CPC .......... *A61N 2005/0652* (2013.01); *A61B 2018/00791* (2013.01); *A61N 2005/0602* (2013.01); *A61N 2005/0666* (2013.01)
USPC .......... 607/88; 607/89; 606/3; 606/7; 606/14; 604/20

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,643,334 A * | 7/1997 | Eckhouse et al. ............ 607/88 |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,976,175 A * | 11/1999 | Hirano et al. ............ 607/89 |
| 5,983,141 A | 11/1999 | Sluijter et al. |
| 6,004,269 A | 12/1999 | Crowley et al. |
| 6,009,877 A | 1/2000 | Edwards |
| 6,066,134 A | 5/2000 | Eggers et al. |
| 6,086,558 A * | 7/2000 | Bower et al. ............ 604/96.01 |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,411,852 B1 * | 6/2002 | Danek et al. ............ 607/42 |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,539,944 B1 * | 4/2003 | Watson ............ 128/898 |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,845,267 B2 | 1/2005 | Harrison et al. |
| 6,850,801 B2 | 2/2005 | Kieval et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 6,953,457 B2 * | 10/2005 | Farr et al. ............ 606/15 |
| 7,122,568 B1 * | 10/2006 | Allison et al. ............ 514/410 |
| 7,149,574 B2 | 12/2006 | Yun et al. |
| 7,162,303 B2 | 1/2007 | Levin et al. |
| 7,221,979 B2 | 5/2007 | Zhou et al. |
| 7,252,677 B2 * | 8/2007 | Burwell et al. ............ 607/88 |
| 7,353,829 B1 * | 4/2008 | Wachter et al. ............ 128/898 |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0165532 A1 | 11/2002 | Hill et al. |
| 2002/0183682 A1 | 12/2002 | Darvish et al. |
| 2003/0004501 A1 * | 1/2003 | Wilkens et al. ............ 606/9 |
| 2003/0050681 A1 | 3/2003 | Pianca et al. |
| 2003/0060858 A1 | 3/2003 | Kieval et al. |
| 2003/0082101 A1 * | 5/2003 | Taylor et al. ............ 424/1.11 |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0044304 A1 | 3/2004 | Hill et al. |
| 2004/0215186 A1 | 10/2004 | Cornelius et al. |
| 2005/0004550 A1 * | 1/2005 | Sun et al. ............ 604/501 |
| 2005/0080409 A1 | 4/2005 | Young et al. |
| 2005/0187579 A1 | 8/2005 | Danek et al. |
| 2005/0228460 A1 | 10/2005 | Levin et al. |
| 2006/0085053 A1 * | 4/2006 | Anderson et al. ............ 607/94 |
| 2006/0095029 A1 | 5/2006 | Young et al. |
| 2006/0100618 A1 | 5/2006 | Chan et al. |
| 2006/0135870 A1 | 6/2006 | Webler |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0264288 A1 * | 11/2007 | Manstein ............ 424/400 |
| 2007/0265687 A1 | 11/2007 | Deem et al. |
| 2008/0139992 A1 * | 6/2008 | Bornstein ............ 604/20 |
| 2008/0221560 A1 * | 9/2008 | Arai et al. ............ 606/14 |
| 2008/0319513 A1 | 12/2008 | Pu et al. |
| 2009/0036948 A1 | 2/2009 | Levin et al. |
| 2009/0054883 A1 * | 2/2009 | Stolen et al. ............ 606/14 |
| 2009/0105791 A1 * | 4/2009 | McGinnis et al. ............ 607/88 |
| 2009/0171337 A1 * | 7/2009 | Paul et al. ............ 606/33 |
| 2009/0299263 A1 * | 12/2009 | Bornstein ............ 604/20 |
| 2009/0299441 A1 * | 12/2009 | Bornstein ............ 607/89 |
| 2010/0041133 A1 * | 2/2010 | Hyde et al. ............ 435/325 |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2011/0092781 A1 * | 4/2011 | Gertner ............ 600/301 |
| 2011/0104061 A1 * | 5/2011 | Seward ............ 424/9.1 |
| 2011/0118725 A1 * | 5/2011 | Mayse et al. ............ 606/33 |
| 2011/0257641 A1 * | 10/2011 | Hastings et al. ............ 606/15 |
| 2011/0264086 A1 * | 10/2011 | Ingle ............ 606/33 |
| 2011/0295343 A1 * | 12/2011 | Bornstein et al. ............ 607/88 |
| 2012/0065494 A1 * | 3/2012 | Gertner et al. ............ 600/411 |
| 2012/0130289 A1 | 5/2012 | Demarais et al. |
| 2012/0130345 A1 | 5/2012 | Levin et al. |
| 2012/0134975 A1 * | 5/2012 | Hyde et al. ............ 424/93.73 |
| 2012/0172837 A1 | 7/2012 | Demarais et al. |
| 2013/0066282 A1 | 3/2013 | Dalton et al. |
| 2013/0066283 A1 * | 3/2013 | Alster et al. ............ 604/294 |

(56) References Cited

U.S. PATENT DOCUMENTS

| | | | |
|---|---|---|---|
| 2013/0165844 A1 | 6/2013 | Shuros et al. | |
| 2013/0324909 A1* | 12/2013 | Aydt et al. | 604/20 |

FOREIGN PATENT DOCUMENTS

| | | |
|---|---|---|
| WO | WO-99/00060 | 1/1999 |
| WO | WO-0122897 | 4/2001 |
| WO | WO-0170114 | 9/2001 |
| WO | WO2004082736 | 9/2004 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2007008954 | 1/2007 |
| WO | WO2008055159 | 5/2008 |
| WO | WO-2014005001 | 1/2014 |

OTHER PUBLICATIONS

DDSA Pharmaceuticals Limited, Oxytetracycline 250 mg Tablets, Package Leaflet, 2008.*

Balasaraswathy et al., UVA and UVB in sunlight, optimal utilization of UV rays in sunlight for phototherapy, Indian J Dermatol Venereol Leprol., Jul.-Aug. 2002; 68 (4): 198-201.*

Murphy-Chutorian et al., Selective absorption of ultraviolet laser energy by human atherosclerotic plaque treated with tetracycline, Am J Cardiol., May 1985.*

Seidlitz et al., Use of Tetracyclines for Bone Metastases, Cancer Drug Discovery and Development Bone Metastasis: Experimental and Clinical Therapeutics, 2005, pp. 293-303.*

Quintero et al., Mechanisms of photosensitization induced by drugs: A general survey, Ars Pharmaceutica, 41:1; 27-46, 2000.*

Levine J.I., Medications that increase sensitivity to light, HHS Publication FDA, Dec. 1990.*

Martin et al., Role of Oxygen Radicals in the Phototoxicity of Tetracyclines toward *Escherichia coli* B, Journal of Bacteriology, Jun. 1987, p. 2516-2522.*

Hasan et al., Phototoxicity of the tetracyclines: Photosensitized emission of singlet delta dioxygen, Proc. Natl. Acad. Sci. USA, vol. 83, pp. 4604-4606, Jul. 1986.*

Bjellerup et al., Influence of tetracycline phototoxicity on the growth of cultured human fibroblasts, The Journal of Investigative Dermatology, 1985.*

European Search Report for European Application No. 13159256, Date Mailed: Oct. 17, 2013, 6 pages.

Zheng et al., "Comparison of the temperature profile and pathological effect at unipolar, bipolar and phased radiofrequency current configurations," Journal of Interventional Cardiac Electrophysiology, 2001, pp. 401-410.

International Search Report and Written Opinion for International App. No. PCT/US2013/048535, Mailed Sep. 16, 2013, 12 pages.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter," Journal of the American College of Cardiology, 1999; 33; pp. 972-984.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, http://clinicaltrials.gov/ct2/show/NCT01628198.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Opposition to European Patent No. EP2092957, Granted Jan. 5, 2011, Date of Opposition Oct. 5, 2011, 26 pages.

OZ, Mehmet, Pressure Relief, TIME, Jan. 9, 2012, 2 pages. <www.time.come/time/printout/0,8816,2103278,00.html>.

Papademetriou, Vasilios, Renal Sympathetic Denervation for the Treatment of Difficult-to-Control or Resistant Hypertension, Int. Journal of Hypertension, 2011, 8 pages.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Purerfellner, Helmut et al., Pulmonary Vein Stenosis Following Catheter Ablation of Atrial Fibrillation, Curr. Opin. Cardio. 20 :484-490, 2005.

Schneider, Peter A., "Endovascular Skills—Guidewire and Catheter Skills for Endovascular Surgery," Second Edition Revised and Expanded, 10 pages, (2003).

ThermoCool Irrigated Catheter and Integrated Ablation System, Biosense Webster (2006), 6 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Allen, E. V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hemaluria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, The American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

(56) References Cited

OTHER PUBLICATIONS

Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards$^{TM}$" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al. "Treatment of renal failure and hypertension." U.S. Appl. No. 60/442,970, Jan. 29, 2003, 23 pages.

(56) References Cited

OTHER PUBLICATIONS

Gertner, Jon, "Meet the Tech Duo That's Revitalizing The Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal Clenervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Beale et al., "Minimally Invasive Treatment for Varicose Veins: A Review of Endovenous Laser Treatment and Radiofrequency Ablation". Lower Extremity Wounds 3(4), 2004, 10 pages.
Miller, Reed, "Finding a Future for Renal Denervation With Better Controlled Trials." Pharma & Medtech Business Intelligence, Article # 01141006003, Oct. 6, 2014, 4 pages.

(56) References Cited

OTHER PUBLICATIONS

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Doumas, Michael et al., "Renal Nerve Ablation for Resistant Hypertension: The Dust Has Not Yet Settled." The Journal of Clinical Hypertension. 2014; vol. 16, No. 6, 2 pages.

Messerli, Franz H. et al. "Renal Denervation for Resistant Hypertension: Dead or Alive?" Healio: Cardiology today's Intervention, May/Jun. 2014, 2 pages.

Dole et al., "Effects of Photodynamic Therapy on Peripheral Nerve: In Situ Compound-Action Potentials Study in a Canine Model." Photomed Laser Surg. Apr. 2005; 23(2): 8pages.

* cited by examiner

DEVICES AND METHODS FOR PHOTODYNAMICALLY MODULATING NEURAL FUNCTION IN A HUMAN

CROSS-REFERENCE TO RELATED APPLICATION(S)

The present application claims priority to U.S. Provisional Patent Application No. 61/666,687, filed Jun. 29, 2012, entitled "DEVICE AND METHOD FOR VASCULAR DELIVERY OF PHOTODYNAMIC THERAPY FOR MODULATING NEURAL FUNCTION," which is incorporated herein in its entirety by reference.

TECHNICAL FIELD

The present technology relates to modulation of neural function, such as localized tissue denervation, using photodynamic methods and devices.

BACKGROUND

The sympathetic nervous system (SNS) is a primarily involuntary control system typically associated with stress responses. SNS tissue fibers are present in almost every organ system of the human body and can affect characteristics such as pupil diameter, gut motility, and urinary output. Such regulation can have adaptive utility in maintaining homeostasis or preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, volume overload states (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys is often found in these patients. Heightened SNS activation commonly characterizes both chronic and end stage renal disease. In patients with end stage renal disease, NE plasma levels above the median have been demonstrated to be predictive of cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate that result from renal sympathetic efferent stimulation are likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal artery have been shown to reduce blood pressure in patients with treatment-resistant hypertension (e.g., radiofrequency, cryogenic or ultrasound ablation of renal nerves).

These devices seek to at least partially disrupt neural function of nerves located in adventitial tissue around the renal artery to achieve a therapeutic reduction in systemic blood pressure. Each of these approaches damages or destroys the neural tissue in the outer layers around the artery, and thus they also affect the intimal, medial, and adventitial layers of the artery to varying extents since the energy or temperature gradient must first transverse the non-neural tissues to reach the intended target.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
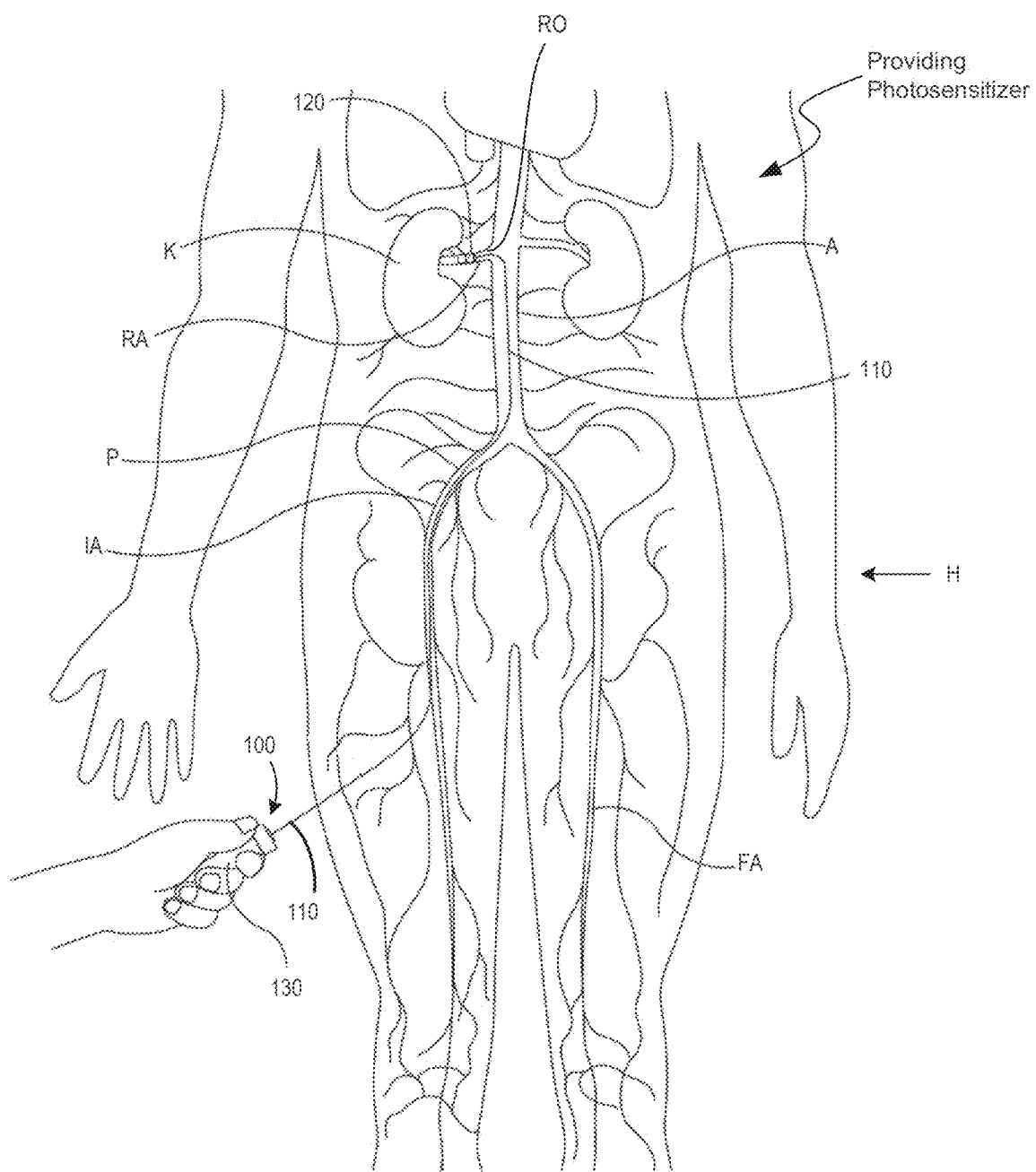
FIG. 1 is a partially cross-sectional anatomical front view illustrating several embodiments of a method for a therapeutic neural modulation in a human in accordance with the present technology.

Specific details of several embodiments of the technology are described below with reference to FIGS. 1-14. Although many of the embodiments are described below with respect to systems, devices, and methods for renal neuromodulation using photodynamic therapies, other applications and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-14.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

Renal neuromodulation is the partial or complete incapacitation or other effective disruption of nerves innervating the kidneys (e.g., rendering neural fibers inert or inactive or otherwise completely or partially reduced in function). For example, renal neuromodulation can include inhibiting, reducing, disrupting, and/or blocking neural communication along neural fibers innervating the kidneys (i.e., efferent and/or afferent nerve fibers). Such incapacitation can be long-term (e.g., permanent or for periods of months, years, or decades) or short-term (e.g., for periods of minutes, hours, days, or weeks). Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis and sudden death, among others. The reduction of afferent neural signals typically contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and body structures innervated by sympathetic nerves. For example, a reduction in central sympathetic drive may reduce insulin resistance that afflicts patients with metabolic syndrome and Type II diabetics.

Several embodiments of the present technology selectively disrupt, and in many instances destroy, perivascular nerves without adversely impairing the function of the non-neural tissues of the blood vessel (e.g., intimal, medial and adventitial tissues of the blood vessel). For example, several embodiments of methods for therapeutic neural modulation in a human can include administering a photosensitizer to a human that preferentially accumulates at selected nerves compared to other tissues proximate the selected nerves. For example, more of the photosensitizer can accumulate in perivascular nerves around a blood vessel than in the non-neural tissues of the blood vessel. The mechanisms for preferentially accumulating the photosensitizer at the nerves can include faster uptake by the nerves, longer residual times at the nerves, or a combination of both. After a desired dosage of the photosensitizer has accumulated at the nerves, the photosensitizer is irradiated using a treatment device positioned within the human. The treatment device delivers radiation to the target nerves at a wavelength that causes the photosensitizer to react such that it damages or disrupts the nerves. For example, the photosensitizer can become toxic upon exposure to the radiation. Because the photosensitizer preferentially accumulates at the nerves and not the other tissue proximate the nerves, the toxicity and corresponding damage is localized primarily at the nerves. Several embodiments of the present technology are expected to be particularly useful for denervation of perivascular nerves while protecting the non-neural tissue of the blood vessel.

Selected Embodiments of Photodynamic Neuromodulation Methods and Devices

FIG. 1 is a partially cross-sectional anatomical front view illustrating several embodiments of methods for therapeutic neural modulation in a human (H). An embodiment includes providing a photosensitizer to neural tissue associated with sympathetic neural activity. Several embodiments of the methods include providing the photosensitizer to perivascular nerves, but other embodiments include providing the photosensitizer to nerve ganglia, peripheral nerves, and spinal nerves. The photosensitizer, for example, can be administered either orally or by injecting the photosensitizer into the human (H). For example, the photosensitizer can be injected directly into the vasculature for systemic distribution, or the photosensitizer can be injected into tissue proximate the target nerves using appropriately sized needles for localized application. In other embodiments, the photosensitizer can be delivered from within the body lumen using an intravascular device. In any of these embodiments, the photosensitizer is selected to preferentially accumulate at the nerves as described in more detail below.

FIG. 1 further illustrates delivering a treatment device 100 having a shaft 110 and a radiation unit 120 at a distal end of the shaft 110 positioned within the vasculature of the patient. Intravascular delivery of the radiation unit 120 can include percutaneously inserting a guide wire (not shown) within the vasculature at an access site (e.g., the femoral, brachial, radial, or axillary artery). The shaft 110 and the radiation unit 120 are moved along the guide wire in a low-profile delivery state until at least a portion of the radiation unit 120 reaches a desired treatment location. The shaft 110 and the radiation unit 120 can include a guide wire lumen configured to receive a guide wire in an over-the-wire or rapid exchange configuration. As illustrated, a section of the proximal portion of a shaft 110 can be extracorporeally positioned and manipulated by an operator via an actuator 130 to advance the shaft 110 and radiation unit 120 along an intravascular path (P) and remotely manipulate a distal portion of the shaft 110.

The positioning and manipulation of the radiation unit 120 can be carried out using computed tomography (CT), fluoroscopy, intravascular ultrasound (IVUS), optical coherence tomography (OCT), intercardiac echocardiography (ICE), combinations thereof, or other suitable guidance modalities. For example, a fluoroscopy system including a flat-panel detector, x-ray or c-arm can rotated to accurately visualize and identify the target treatment site. Other embodiments can include locating the treatment site using IVUS, OCT and other suitable imaging mapping modalities that can correlate the target treatment site with an identifiable anatomical structure (e.g., a spinal feature) and/or a radiopaque ruler positioned under or on the patient before delivering the radiation unit 120 to the target site. Further, in some embodiments, image guidance components (e.g., IVUS or OCT) may be integrated with the treatment device 100 and/or running parallel with the treatment device 100 to provide image guidance during positioning of the radiation unit 120. This can be carried out by coupling IVUS, OCT or other image-guidance components to a distal portion of the shaft 100 to provide three-dimensional images of the vasculature proximate to the target site to facilitate positioning or deploying the radiation unit 120 within the target blood vessel. In the specific example shown in FIG. 1, the radiation unit 120 is positioned in the renal artery (RA) at a suitable location between the renal ostium (RO) and the kidney (K).

After the radiation unit 120 has been positioned at a treatment location, the radiation unit 120 can be transformed or otherwise manipulated from a low-profile delivery state suitable for passing through the vasculature (e.g., the femoral artery (FA), the iliac artery (IA), and aorta (A)) to a deployed state in a target vessel (e.g., the renal artery (RA)). In the deployed state, for example, the radiation unit 120 can securely contact the wall of the blood vessel or other body lumen to stabilize the radiation unit 120 for delivering energy to the target nerves. In some embodiments, the radiation unit 120 may be delivered to a treatment site using a guide sheath (not shown) with or without using a guide wire. When the radiation unit 120 is at the target site, the guide sheath may be at least partially withdrawn or retracted so that the radiation unit 120 can transform to the deployed state. For example, the radiation unit 120 can have a balloon, basket, spiral member (e.g., helical), or other suitable positioning member that can be inflated, self-expanded, or manipulated by a wire to move from the delivery state to the deployed state. In some other embodiments, the shaft 110 may itself be steerable such that the radiation unit 120 can be delivered to the treatment site without the aid of a guide wire and/or guide sheath.

Figure 2:
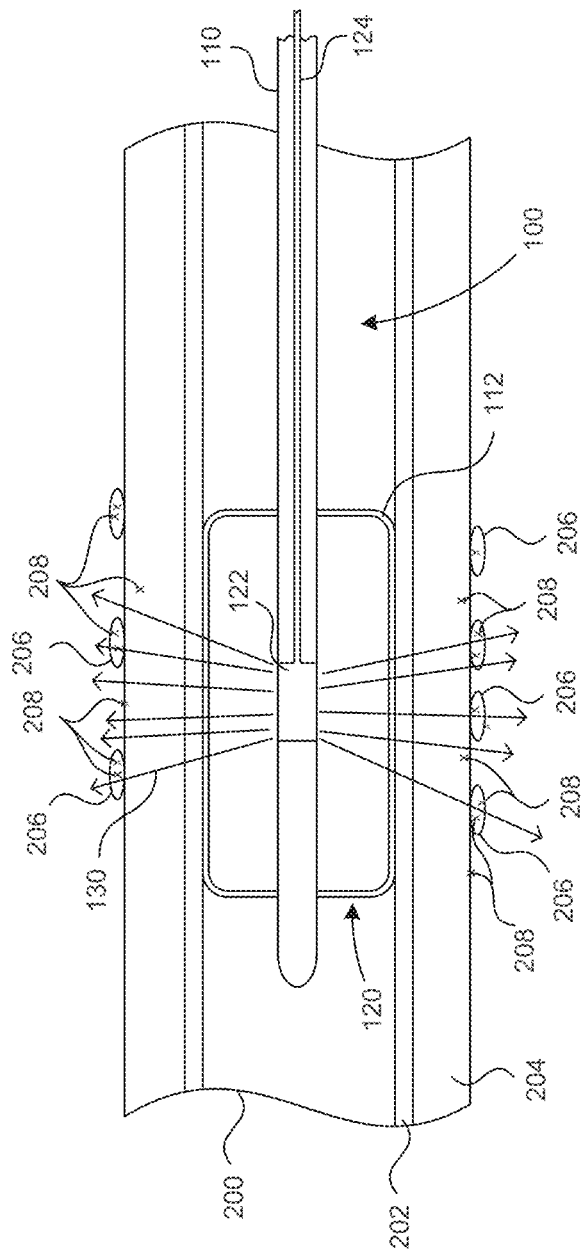
FIG. 2 is a schematic cross-sectional view of a distal portion of a treatment device at a target site in a blood vessel in accordance with the present technology.

FIG. 2 is a schematic cross-sectional view of a distal portion of the treatment device 100 at a target site in a body lumen 200, such as a blood vessel, airway, or other naturally occurring passageway. The radiation unit 120 can include a positioning member 112 at the distal end of a shaft 110 and an emitter 122. The positioning member 112 can be expanded to contact the inner wall of the body lumen 200 such that the emitter 122 is positioned at a desired location relative to the target site. The positioning member 112, for example, can be a balloon, basket, spiral member, or other structure. In one embodiment, the emitter 122 is an optical element coupled to a fiber optic line 124 that extends to an external radiation source. In other embodiments, the emitter 122 itself can be a radiation source coupled to an electrical lead that generates the radiation from within the body lumen 200. For example, the emitter 122 can be a light emitting diode (LED) or an array of LEDs. When the emitter 122 is centered in the body lumen as shown in FIG. 2, the positioning member 112 is generally expanded using an inflation medium that does not overly attenuate the energy of the radiation such that the positioning member contacts the inner wall of the body lumen so that blood does not absorb the energy of the radiation.

FIG. 2 further illustrates an embodiment of the operation of the treatment device 100. After the positioning member 112 has been transformed into the deployed state in which it contacts at least a portion of the inner wall of the body lumen 200, radiation 130 is delivered from the emitter 122. The radiation 130 passes through the positioning member 112, tissue 202 and 204 of the inner wall of the body lumen 200, and nerves 206 in the tissue around the body lumen 200. When the body lumen 200 is a blood vessel, such as the renal artery, tissue 202 can be the intimal tissue, tissue 204 can be the medial tissue, and the nerves 206 can be the renal nerves. The radiation 130 is applied to the nerves 206 after a sufficient quantity of the photosensitizer 208 has accumulated at the nerves 206 and either before an undesirable amount of the photosensitizer has accumulated in and/or in the tissues 202 and 204 or after a sufficient quantity of photosensitizer 208 has dissipated from the tissues 202 and 204. In several embodiments, the photosensitizer 208 can accumulate in and/or on the nerves 206 by preferentially binding to the nerves 206 as shown schematically in FIG. 2. The radiation 130 causes to the photosensitizer 208 to react such that the photosensitizer 208 damages or otherwise disrupts at least the nerves 206. For example, the photosensitizer 208 can become toxic to the nerves 206 and possibly the other tissues proximate the nerves 206. Since the concentration of the photosensitizer 208 is greater at the nerves 206 than the tissues 202 and 204, greater damage is caused to the nerves 206. Thus, several embodiments for therapeutically modulating perivascular nerves in a human in accordance with the present technology selectively disrupt the perivascular nerves such that neural communication is at least partially inhibited along the targeted perivascular nerves without disrupting the function of the other tissues of the wall of the blood vessel.

Selected Embodiments of Photosensitizers and Dosages

The photosensitizer 208 can be any suitable compound that preferentially accumulates at neural tissue compared to other tissues proximate the nerves. For example, the photosensitizer 208 can accumulate in and/or on the neural tissue over a period of time to a greater extent than other tissue proximate the neural tissue. In one embodiment, the photosensitizer can be oxytetracycline, a suitable tetracycline analog, or other suitable photosensitive compounds that preferentially bind to neural tissue. Oxytetracycline is expected to preferentially bind to calcium in the nerves such that more oxytetracycline remains at the nerves than in the non-neural tissue proximate to the nerves after a sufficient period of time has elapsed after administering the oxytetracycline.

When the photosensitizer 208 is oxytetracycline, the radiation delivered from the emitter 122 has a wavelength of 350 nm-365 nm, and often more specifically 351 nm-355 nm. In one particular embodiment, the oxytetracycline is administered at a dosage of 0.5-1 mg/kg, and in other embodiments the oxytetracycline can be administered at a dosage of 1-49 mg/kg, 50-300 mg/kg, or 300-600 mg/kg. The radiation can have a dosage of 0.5-5 J/cm$^2$, 5-25 J/cm$^2$, 25-100 J/cm$^2$, or 100-500 J/cm$^2$ depending on a number of parameters such as the thickness and type of tissue between the radiation emitter and the target neural tissue, and the radiation can be continuous or pulsed irradiation exposure. In the case of pulsed radiation, the pulse rate can be approximately 10-50 ps, 15-40 ps, 20-30 ps, or 20-25 ps (e.g., 24 ps). The oxytetracycline can be administered approximately 30-180 minutes, or 3-24 hours, before being irradiated with radiation at a wavelength of approximately 351 nm-365 nm.

In another example, the photosensitizers can be furocoumarins (psoralens) or porphyrins administered at a dosage of 0.5-1 mg/kg, 1-49 mg/kg, 50-300 mg/kg, or 300-600 mg/kg. Approximately 30-180 minutes, or 3-24 hours, after administering the furocoumarins (psoralens) or porphyrins, a radiation dosage of 0.5-5 J/cm$^2$, 5-25 J/cm$^2$, 25-100 J/cm$^2$, or 100-500 J/cm$^2$ is delivered to the target site.

In another example, the photosensitizers can be benzoporphyrin or a derivative of benzoporphyrin (such as lemuteporfin) administered at a dosage of 0.5-1 mg/kg, 1-49 mg/kg, 50-300 mg/kg, or 300-600 mg/kg. Approximately 30-180 minutes, or 3-24 hours, after administering the lemuteporfin, a radiation dosage of 0.5-5 J/cm², 5-25 J/cm², 25-100 J/cm², or 100-500 J/cm² is delivered to the target site.

In another example, the photosensitizers can be phthalocyanines administered at a dosage of 0.5-1 mg/kg, 1-49 mg/kg, 50-300 mg/kg, or 300-600 mg/kg. Approximately 30-180 minutes, or 3-24 hours, after administering the lemuteporfin, a radiation dosage of 0.5-5 J/cm², 5-25 J/cm², 25-100 J/cm² or 100-500 J/cm² is delivered to the target site.

Additional Embodiments of Photodynamic Neuromodulation Devices

Figure 3A:
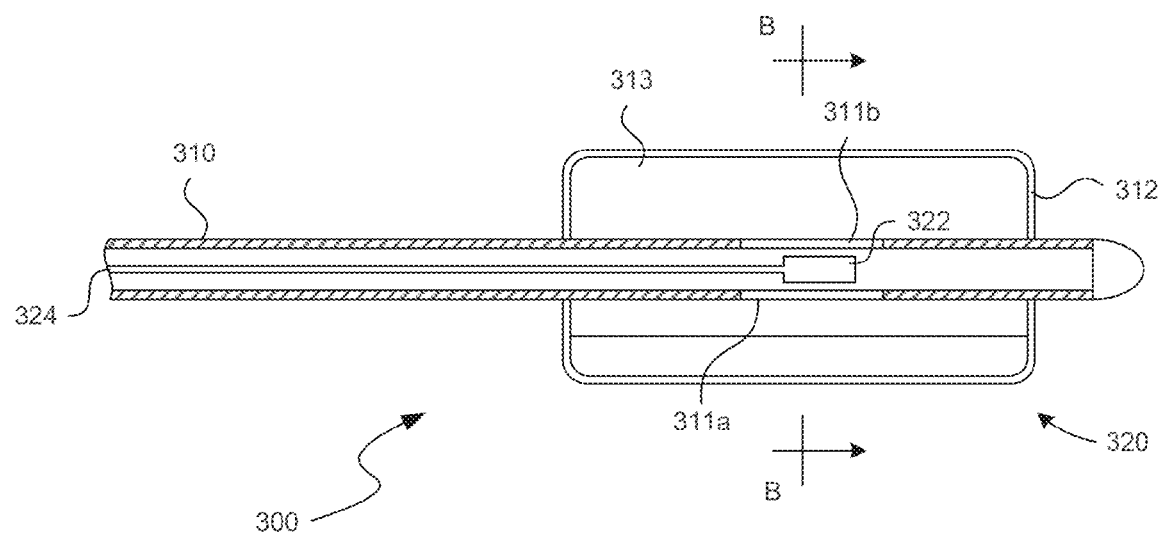
FIG. 3A is a schematic cross-sectional view of a distal portion of a treatment device in accordance with the present technology.
Figure 3B:
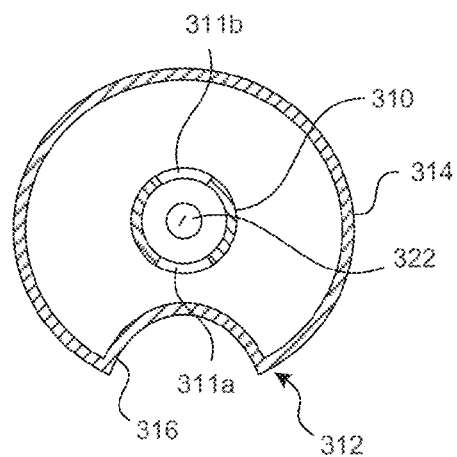
FIG. 3B is a cross-sectional view of the treatment device taken along line B-B of FIG. 3A.

FIG. 3A is a schematic cross-sectional view of a treatment device 300 for therapeutic neuromodulation in accordance with the present technology, and FIG. 3B is a cross-sectional view of the treatment device 300 taken along line B-B of FIG. 3A. Referring to FIG. 3A, the treatment device 300 can include an elongated shaft 310 having a plurality of openings 311a-b and a radiation unit 320 attached to a distal portion of the shaft 310. The radiation unit 320 can include a positioning member 312 attached to the shaft 310 and an emitter 322 configured to deliver radiation through the openings 311a-b such that the radiation projects radially outward with respect to the shaft 310. The radiation passes through a chamber 313 defined by the positioning element 312 to irradiate the target tissue as explained above. The emitter 322 can be an optical element coupled to a fiber optic cable 324 that directs the light in the desired radial distribution relative to the shaft 310. The radiation source in such embodiments can be positioned at an extracorporeal location and configured to direct light through the fiber optic cable 324 to the emitter 322. In other embodiments, the emitter 322 can be an internal radiation source, such as an LED or other small radiation emitter. The emitter 322, for example, can be an array of one or more LEDs that emit radiation in a desired bandwidth.

Referring to FIG. 3B, the positioning element 312 can be an inflatable balloon having a first portion 314 configured to contact an inner wall of a blood vessel or another body lumen in a deployed state. For example, other body lumens can be the esophagus, trachea, lung airways, and/or the gastro-intestinal system. The first section 314 is configured to securely position the emitter 322 at a desired location with respect to the target tissue in the deployed state. The positioning element 312 can further include a second portion 316 defining a channel or other external passageway configured to allow blood, air, or another body fluid to pass through the channel when the positioning element 312 is in the deployed state (e.g., inflated or expanded to securely position the emitter 322 at a desired location with respect to the target tissue). The radiation emitter 320 is expected to be particularly useful for applications in the renal artery because it only partially occludes the blood vessel to allow blood flow during the procedure. This will allow exposure times longer than the 2-5 minutes that the renal arteries can be occluded, if necessary.

Figure 4:
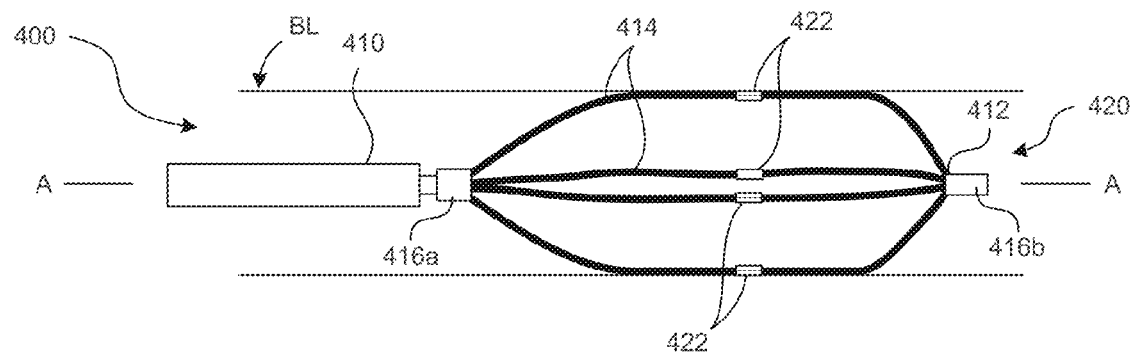
FIG. 4 is a partial cross-sectional view of a distal portion of a treatment device for therapeutic neural modulation in accordance with an embodiment of the present technology.

FIG. 4 is a schematic cross-sectional view of another embodiment of a treatment device 400 in accordance with the present technology for therapeutically modulating neural function. The treatment device 400 can include an elongated shaft and a radiation unit 420 having a positioning member 412 defined by an expandable basket having a plurality of supports 414. The proximal ends of the supports 414 are attached to a proximal hub 416a, and the distal end of the supports 414 are attached to a distal hub 416b. At least one of the proximal and distal hubs 416a and 416b is moveable along the longitudinal dimension of the shaft 410 to transform the positioning member 412 from a low-profile delivery state to an expanded deployed state in which the supports 414 contact in inner wall of a body lumen (BL) at a target site. The radiation unit 420 further includes a plurality of radiation emitters 422 attached to the supports 414. The radiation emitters 422 can be optical elements coupled to fiber optic cables for delivering radiation from a radiation source at an extracorporeal location to the target tissue at the body lumen (BL). In other embodiments, the radiation emitters 422 can be internal radiation sources, such as LEDs, that are electrically coupled to a power source at an extracorporeal location via electrical leads within the shaft 410. In the embodiment shown in FIG. 4, the radiation emitters 422 are angularly spaced apart from each other around a longitudinal dimension A-A of the shaft 410 at a common area along the length of the longitudinal dimension A-A. This arrangement of radiation emitters 422 provides a circumferential exposure in a common plane perpendicular to the longitudinal dimension A-A of the shaft 410.

In operation, a photosensitizer is administered to the patient as described above and the treatment device 400 is positioned at the target site with the supports 414 in the low-profile delivery state. The supports 414 are expanded to the deployed state such that the radiation emitters 422 contact the inner wall of the body lumen (BL) or are positioned apart from the inner wall of the body lumen depending on the type of fluids within the body lumen. For example, in the case of blood vessels or other body lumens with fluids that attenuate the radiation, the supports are generally expanded such that the emitters 422 contact the vessel wall to directly irradiate the inner wall of the vessel so that blood does not block the radiation. Radiation is then delivered to the target neural tissue from the radiation emitters 422 to react the photosensitizer as described above.

Figure 5:
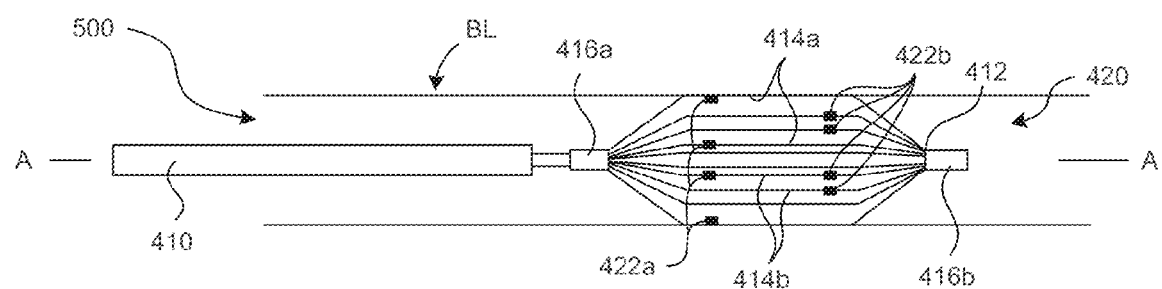
FIG. 5 is a partial cross-sectional view of a distal portion of a treatment device for therapeutic neural modulation in accordance with an embodiment of the present technology.

FIG. 5 is a cross-sectional view of another embodiment of a treatment device 500 in accordance with the present technology for delivering radiation to target tissue. The treatment device 500 can be similar to the treatment device 400 shown in FIG. 4, and like reference numbers refer to similar or identical components in these figures. Referring to FIG. 5, the treatment device 500 has one or more proximal radiation emitters 422a coupled to first supports 414a and one or more distal radiation emitters 422b coupled to second supports 414b. The proximal and distal radiation emitters 422a and 422b are spaced longitudinally apart from each other along the length of the longitudinal dimension A-A of the shaft 410, and the proximal and distal radiation emitters 422a and 422b are also angularly offset from each other relative to the longitudinal dimension A-A. Although eight supports 414 and eight radiation emitters 422 are shown in FIG. 5, any suitable number supports and emitters may be used. For example, the treatment device 500 may have two first supports 414a, two first proximal radiation emitters 422a (one on each first support 414a), two second supports 414b, and two distal radiation emitters 422b (one on each second support 414b). Such a configuration of proximal and distal radiation emitters provides angularly offset exposure zones such that the radiation does not completely expose the full circumference of the lumen in a plane perpendicular to the longitudinal dimension A-A of the shaft.

Figure 6:
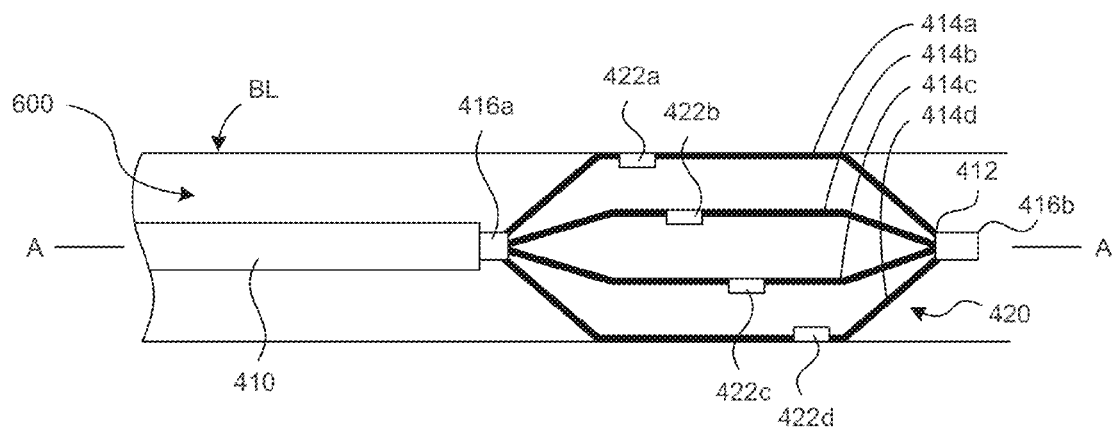
FIG. 6 is a partial cross-sectional view of a distal portion of a treatment device for therapeutic neural modulation in accordance with an embodiment of the present technology.

FIG. 6 is a cross-sectional view of another embodiment of a treatment device 600 in accordance with the present technology. The treatment device 600 is similar to the treatment devices 400 and 500, and like reference numbers refer to similar or identical components in FIGS. 4-6. The treatment device 600 has first-fourth supports 414a-d, respectively, and first-fourth radiation emitters 422a-d, respectively. The radiation emitters 422a-d are spaced apart from each other at different longitudinal and angular locations with respect to the longitudinal dimension A-A of the shaft 410 such that the radiation is delivered to different longitudinal and angular locations along the inner wall of the body lumen (BL). This arrangement of emitters provides another pattern of non-circumferential exposure zones.

The positioning elements 412 of the treatment devices 400, 500 and 600 shown in FIGS. 4-6 can be self-expanding baskets or pull-wire actuated baskets. For example, self-expanding supports 414 can comprise a shape-memory metal, or they can be springs that expand outwardly after being released from a sheath. In pull-wire embodiments, the distal hub 416b can be coupled to a pull-wire to expand the supports 414 outwardly when the pull-wire is retracted proximally.

Figure 7:
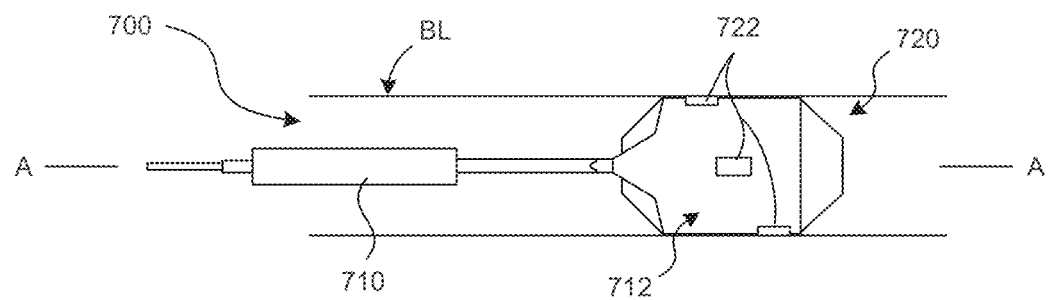
FIG. 7 is a partial cross-sectional view of a distal portion of a treatment device for therapeutic neural modulation in accordance with an embodiment of the present technology.

FIG. 7 is a cross-sectional view of an embodiment of a treatment device 700 for therapeutically modulating neural function in accordance with the technology. The treatment device 700 can include an elongated shaft 710 and a radiation unit 720 having a positioning element 712 at a distal portion of the shaft 710 and a plurality of radiation emitters 722 coupled to the positioning element 712. In the illustrated embodiment, the positioning element 712 is a balloon and the radiation emitters 722 are arranged such that they are spaced apart from each other longitudinally and angularly with respect to the longitudinal dimension A-A of the shaft 710. The device 700 can include a suitable number of radiation emitters 722 depending on the size of the body lumen (BL). For example, 2, 4, 6, 8, 10 or 12 radiation emitters 722 can be spaced apart from each other angularly and/or longitudinally with respect to the longitudinal dimension A-A of the shaft 710 to provide the desired pattern of radiation along the inner wall of the body lumen (BL).

Figure 8:
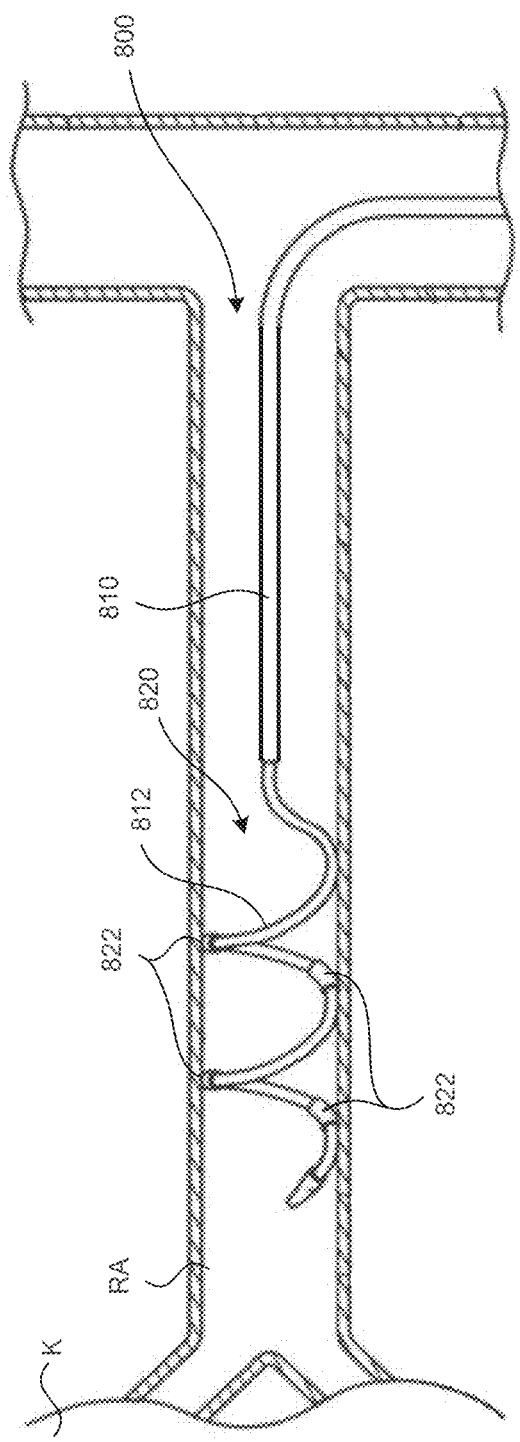
FIG. 8 is a partial cross-sectional view of a distal portion of a treatment device for therapeutic neural modulation in accordance with an embodiment of the present technology.

FIG. 8 is a partial cross-sectional side view of a treatment device 800 for therapeutically modulating neural function in accordance with another embodiment of the present technology. The treatment device 800 includes an elongated shaft 810 and a radiation unit 820 having a positioning member 812 and a plurality of radiation emitters 822 coupled to the positioning member 812. In this embodiment, the positioning member 812 is a self-expanding or pull-wire actuated member that has a substantially linear low-profile delivery state configured to be contained in a sheath and a spiral (e.g., helical) deployed state configured to position in the emitters 812 against the inner wall of the body lumen (BL). The positioning element 812 can be a helix with a constant pitch and diameter, or the helix can have a pitch and/or diameter that varies at different portions along the positioning member 812.

Figure 9:
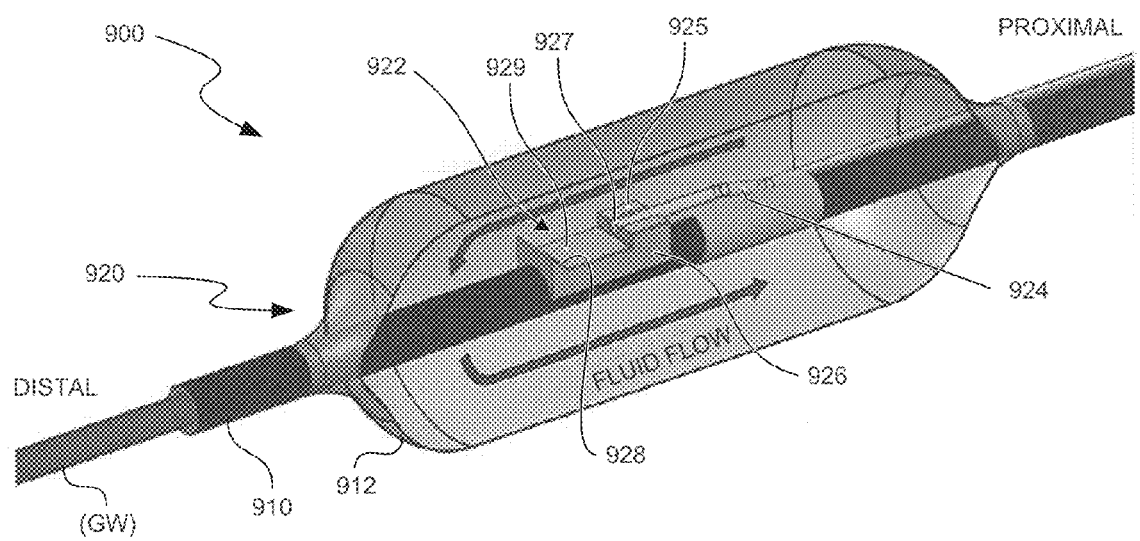
FIG. 9 is an isometric view having a cut-away portion showing a distal portion of a treatment device for therapeutic neuromodulation in accordance with an embodiment of the present technology.

FIG. 9 is an isometric view having a cut-away portion showing a distal portion of a treatment device 900 for therapeutic neuromodulation in accordance with an embodiment of the present technology. The treatment device 900 can include a shaft 910 and a radiation unit 920 attached to a distal portion of the shaft 910. The radiation unit 920 can include a positioning member 912 defined by a balloon and a radiation emitter 922 carried by the shaft 910 within the positioning member 912. The radiation emitter 922 can include a fiber optic cable 924 configured to transmit electromagnetic radiation from a source to the radiation unit 920 and a reflector 925 configured to direct the electromagnetic radiation from the fiber optic cable 924 to target tissue outside of the radiation unit 920. In one embodiment, the reflector 925 has a base 926 mounted to or otherwise carried by the shaft 910, a slot 927 at a proximal end of the base 926 to retain a distal end of the fiber optic cable 924, and an inclined reflective surface 928 configured to direct light transmitted through the fiber optic cable 924 at non-parallel angles (e.g., transverse) to the longitudinal axis of the shaft 910. In one embodiment, the inclined reflective surface 928 is in a plane at an angle of 45° relative to the shaft to direct light through the positioning member 912 perpendicularly to the shaft 910. In other embodiments, the inclined surface 928 can be at other angles to direct the light at transverse angles with respect to the shaft 910. The inclined surface 928 can be spaced apart from the distal terminus of the fiber optic cable 924 by a channel 929.

The reflector 925 can be made of glass, silicon, metals, or other materials covered with reflective materials. In other embodiments, the reflector 925 can be a prism with an inclined surface or other structure that deflects the light in a desired direction. In still other embodiments, the radiation unit 920 may not include the reflector, but instead the fiber optic cable 924 can be bent or have a tip that diverts the radiation at a desired angle with respect to the shaft 910.

The balloon-type positioning member 912 can be filled with a saline solution or other solution through which the light can pass. In one embodiment, the shaft 910 and positioning member 912 are configured to provide fluid flow through the positioning member 912 to cool the tissue being irradiated. Although cooling is not necessary in many embodiments, some photonic methods may cause the tissue of the inner wall of the body lumen to heat to temperatures that can be uncomfortable or otherwise undesirable. The fluid flow through the positioning member 912 is accordingly useful in such situations to maintain the temperature of the inner wall of the body lumen. Additionally, the radiation unit 920 can include a temperature sensor on the positioning member 912 to monitor the temperature of the tissue. The temperature sensor, for example, can be mounted to the surface of a balloon-type positioning member 912 to accurately sense the temperature at the inner wall of the body lumen.

Figure 10:
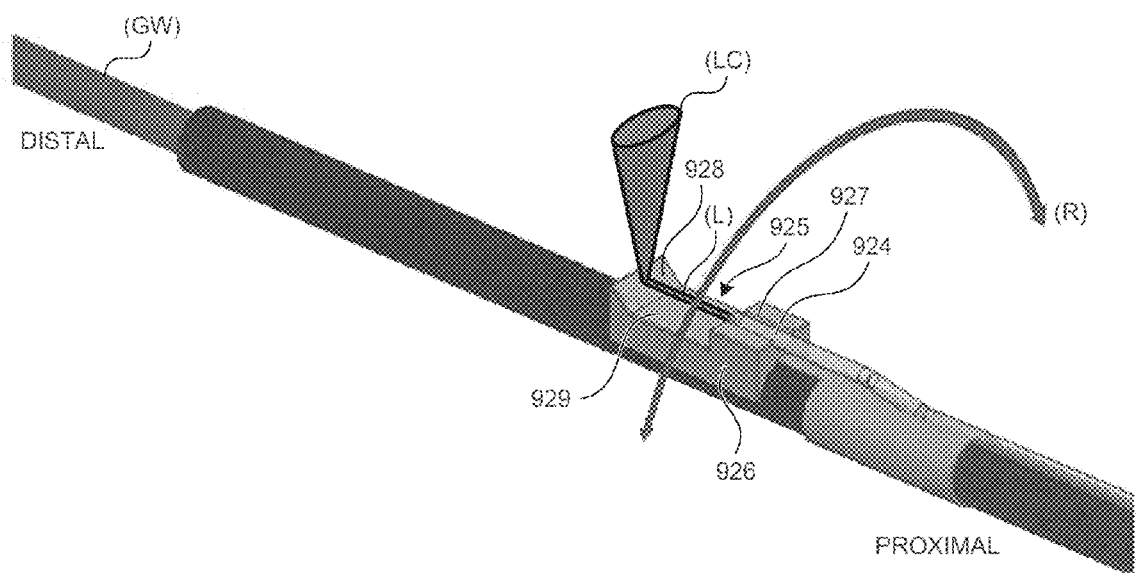
FIG. 10 is an isometric view further illustrating an embodiment of operating the radiation unit.

FIG. 10 is an isometric view further illustrating an embodiment of operating the radiation unit 920. The light (L) is projected from the terminus of the fiber optic cable 924 and reflected from the inclined surface 928 to form a light cone (LC) that projects out of the positioning element 912 (FIG. 9). The light cone (LC) can be rotated such that it continuously scans the full circumference of the inner wall of the body lumen, or the light cone (LC) can irradiate one or more discrete areas of the inner wall. For example, the shaft 910 and the radiation unit 920 can be rotated (R) around a guide wire (GW) such that the light cone (LC) continuously irradiates a full 360° circumference of the body lumen or intermittently irradiates only discrete areas around the circumference of the body lumen. In this embodiment, the positioning member 912 can be freely rotated within the body lumen because the positioning member 912 is inflated so that it substantially occludes the body lumen without contacting the inner wall of the body lumen. In another embodiment, the reflector 925 and the fiber optic cable 924 can be mounted onto a separate shaft that can rotate with respect to the shaft 910. This allows the positioning member 912 to be inflated such that the positioning member 912 contacts the inner wall and remains stationary with respect to the body lumen while the reflector 925 and the fiber optic cable 924 rotate and scan the light cone (LC) around the body lumen. The radiation unit 920 can also be translated along the longitudinal direction of the body lumen and rotated to provide a continuous helical lesion or a plurality of separate lesions having a helical/spiral pattern or other desired pattern.

In another embodiment of the treatment device shown in FIGS. 9 and 10, the radiation unit 920 can include a plurality of fiber optic cables and a corresponding plurality of reflectors 925. For example, two reflectors 925 could be mounted on opposite sides of the shaft 910 and two fiber optic cables 924 could extend along the length of the shaft 910 such that two separate light cones project from opposite sides of the positioning member 912. Similarly, any number of reflectors can be arranged in an array along the length of the shaft 910 and/or around the circumference of the shaft 910 to form a continuous circumferential or spiral lesion, or several lesions in a circumferential, spiral, offset, or other pattern.

The radiation emitters 422, 722, 822 and 922 shown in FIGS. 4-10 can be independently operable to provide a desired radiation pattern. As such, only certain emitters may be active for a particular procedure or for a specific patient. The emitters can be fired simultaneously, or in other embodiments the emitters can be fired sequentially or in different groups or other patterns. Additionally, the radiation units 120, 320, 420, 720, 820 and 920 can be activated at several different locations along the length of a vessel and at different rotational orientations within a vessel. For example, referring to FIG. 1, the radiation unit 120 can be activated at the location shown for a suitable period to sufficiently irradiate the photosensitizer at that location. The radiation unit 120 can then be transformed to a low-profile state, moved distally or proximally along the renal artery (RA) to a different location, transformed to a deployed state, and then re-activated to irradiate another area of the renal artery (RA). The procedure can also be performed in both the left and right renal arteries for a bi-lateral therapy.

Additionally, other embodiments of treatment devices can have a fiber optic cable or an in vivo emitter at a distal tip of the shaft that can be placed against the inner wall of a body lumen to irradiate discrete areas. For example, the device in International Publication No. WO 2008/003058, filed Jun. 28, 2007, and incorporated by reference herein, can be modified to have a fiber optic cable and/or an LED at the distal tip in addition to or in lieu of an electrode.

Figure 11:
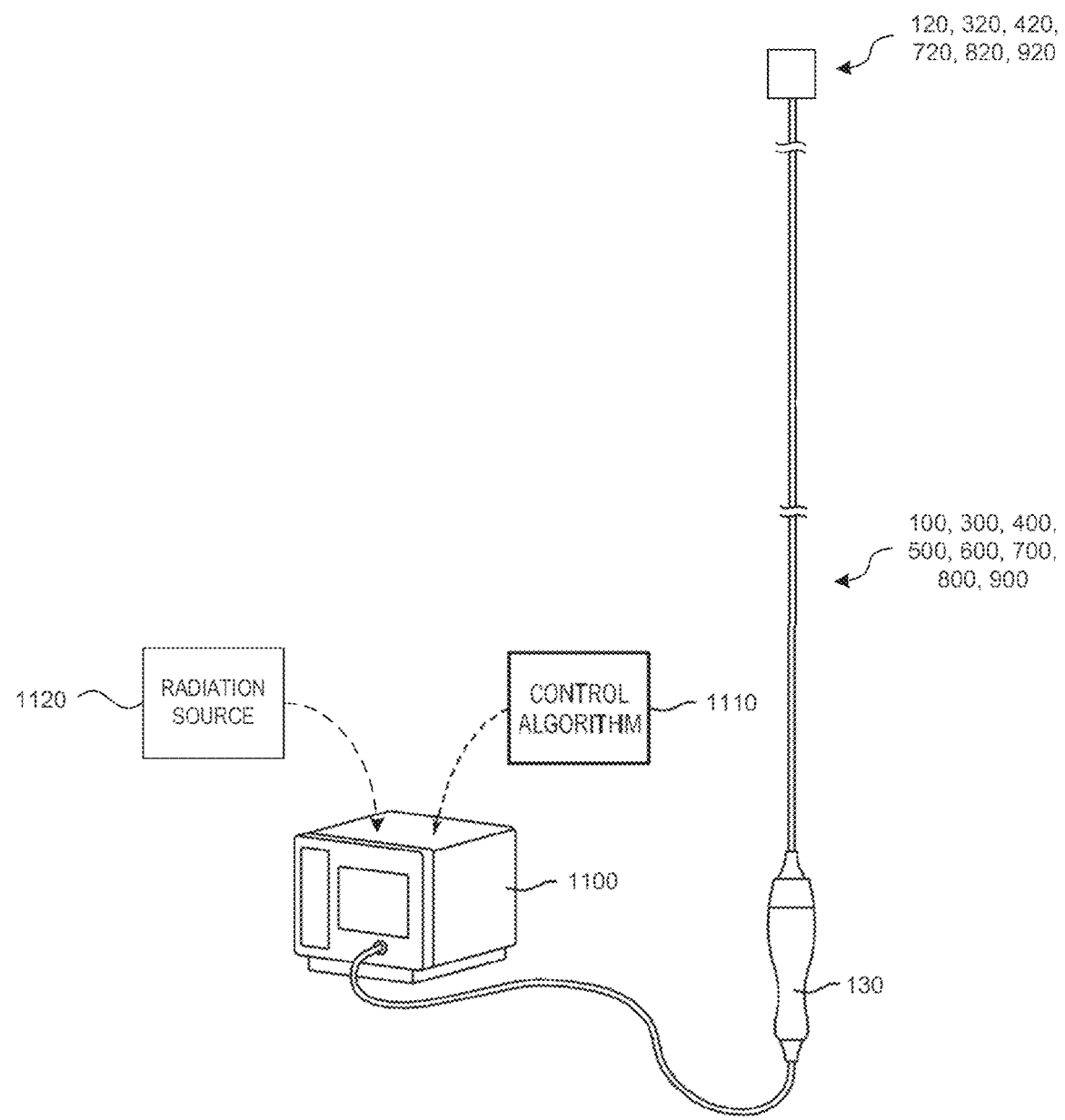
FIG. 11 is schematic view of a system for operating treatment devices for therapeutic neural modulation in accordance with an embodiment of the present technology.

FIG. 11 is a schematic view of a system having a controller 1100 that includes a control algorithm 1110 for operating any of the treatment devices 100, 300, 400, 500, 600, 700, 800 and 900 described above with reference to FIGS. 1-10. The controller 1000 can optionally include a radiation source 1020 that generates the radiation for transmission via fiber optic lines or other light guides through the shaft of the treatment device to the radiation emitters 122, 322, 422, 722, 822 and 922 at the distal end of the shaft. In other embodiments, the controller includes a power source electrically coupled to LED type or other in vivo radiation emitters 122, 322, 422, 722, 822 and 922 at the distal end of the shaft. The algorithm 1110 can include instructions contained on a computer operable medium that operates the radiation emitters to provide the desired radiation pattern and extent of irradiation. In one embodiment, the algorithm 1110 causes the controller 1100 to deliver radiation via the radiation emitter(s) 122, 322, 422, 722, 822 and 922 at a wavelength of 350 nm-365 nm, and in some embodiments within the range of 351 nm-355 nm. The controller 1000 can further cause 0.5-5 J/cm$^2$, 5-25 J/cm$^2$, 25-100 J/cm$^2$, or 100-500 J/cm$^2$ of radiation to be delivered. Any of the foregoing ranges of radiation dosage can be delivered from a single emitter or from each emitter of a plurality of emitters.

Selected Applications, Test Results and Examples

Several embodiments of the present technology can be used intravascularly in the renal arteries, renal ostium, renal veins, renal pelvis, renal calyx (e.g., through the ureter), and/or the renal branch arteries near the renal parenchyma to affect the renal plexus/renal nerve including afferent renal nerves and/or efferent renal nerves. Applications that target the renal plexus/renal nerve through the renal artery, renal ostium and/or renal vein are often directed to treating hypertension, left ventricular hypertrophy, ventricular arrhythmias, sudden cardiac death, insulin resistance, diabetes, metabolic syndrome, hyperaldosteronism, erectile dysfunction, Polycystic Ovary Syndrome (PCOS), infertility (female), Polycystic Kidney Disease (PKD), renal failure, and pain associated with the kidneys. Applications that target efferent renal nerves at the renal pelvis or renal calxy (e.g., through the ureter) can be directed toward decreasing central sympathetic drive to treat hypertension, other cardiac conditions, diabetes, etc. Treatments that target efferent and/or afferent renal nerves at the renal artery and/or the renal branch arteries can be used for treating kidney disease (PKD, renal failure, etc.) and reducing central sympathetic drive (e.g., for treatment of hypertension in patients diagnosed having cystinuria or having an increased risk of developing kidney stones).

Several other non-renal nerve targets, treatment locations, and diseases/conditions/etiologies are listed below in TABLE 1. In each of these additional non-renal applications, the photosensitizer is administered to the patient and the radiation unit of the treatment device is intravascularly positioned at the treatment location to target the nerves for treating the particular disease, condition, and/or etiology as set forth in TABLE 1.

TABLE 1

| Nerve Target | Intravascular treatment location | Disease/Condition/Etiology |
|---|---|---|
| Ovarian plexus/Ovarian Nerve | Ovarian Artery/Vein | PCOS, infertility |
| Spermatic Plexus | Testicular Artery/Vein | Testicular pain (orchialgia) |
| Genital branch of genitofemoral nerve (Lumbar Plexus) | External iliac artery/vein, testicular vessels, | Testicular pain (orchialgia), vasectomy complications, vulvodynia, pain associated with scrotum, |
| Ilioinguinal nerve (Lumbar Plexus) | Deep circumflex iliac artery (or vein) which is a branch of the external iliac artery | Pain associated with injury, scrotal skin, skin over the root of the penis, groin |
| Sacral Plexus | Internal iliac artery, internal iliac vein | Genital (male and female) pain (orchialgia, vulvodynia, clitorodynia, injury) |
| Pudendal nerve (sacral plexus) | Internal pudendal vessels (artery) | Genital (male and female) pain (orchialgia, vulvodynia, clitorodynia), erectile dysfunction |
| Perineal nerve (from pudendal nerve) | Internal pudendal artery | Genital (male and female) pain (orchialgia, vulvodynia, clitorodynia, scrotum) |

TABLE 1-continued

| Nerve Target | Intravascular treatment location | Disease/Condition/Etiology |
|---|---|---|
| Vaginal plexus | Branches of the internal iliac artery (e.g., vaginal arteries, vaginal venous plexus) | Pain or spasm (vaginismus) associated with vagina and clitoris |
| Uterine Plexus | Uterine artery | Uterine pain, vaginal pain, vaginismus |
| Lumbosacral plexus (anterior divisions of the lumbar nerves, sacral nerves, and coccygeal nerve) | Internal iliac artery, internal iliac vein, the ureter, superior gluteal artery and vein | Pain in pelvic region |
| Celiac Plexus | Celiac Artery | Pain in abdominal viscera (pancreas (pancreatitis, pancreatic cancer), Hepatobiliary diseases (liver and biliary tract and gallbladder), spleen (inflammation, leukemia, lymphoma, etc), stomach (cancer), small intestine and large bowel (cancer), kidney) |
| Superior Mesenteric Plexus | Superior Mesenteric Artery/Vein | Pain associated with pancreas (pancreatitis, pancreatic cancer) and small intestine and colon (cancer); treatment of gastrointestinal disorders (inflammatory bowel disease, e.g., Crohn's disease and ulcerative colitis) |
| Hepatic plexus | Hepatic artery | Pain associated with Hepatobiliary diseases (liver and biliary tract and gallbladder) |
| Splenic plexus | Splenic artery/vein, splenic branch arteries | Pain associated with spleen (inflammation, leukemia, lymphoma, etc), treat inflammation (e.g., overactive immune response), inflammation associated with autoimmune diseases (Multiple sclerosis, lupus, psoriasis) |
| Gastric plexus | Gastric artery, superior mesenteric artery/vein, inferior mesenteric artery/vein | Gastrointestinal disorders (inflammatory bowel disease, e.g., Crohn's disease and ulcerative colitis, collagenous colitis, lymphocytic colitis, ischaemic colitis, diversion colitis, and Behcet's disease), obesity, overeating |
| Pancreatic plexus | Pancreatic artery | Pain associated with pancreas (pancreatitis, pancreatic cancer) |

Several embodiments of the present technology are also applicable to extravascular locations. For example, neural structures such as ganglia, peripheral nerves, spinal nerves, cranial nerves, and/or cortical or deep brain neural structures can be modulated in accordance with the present technology. In these embodiments, a neural photosensitizer is administered to the patient and a percutaneous treatment device with a radiation unit is inserted into the patient and positioned proximate to the target neural structures. The treatment device, for example, can be a probe or surgical instrument that can penetrate tissue, and the radiation unit can have a fiber optic emitter and/or internal radiation source at a distal end of the probe. The photosensitizers, radiation, and dosages can be any of the foregoing dosages used for intravascular applications.

Figure 12:
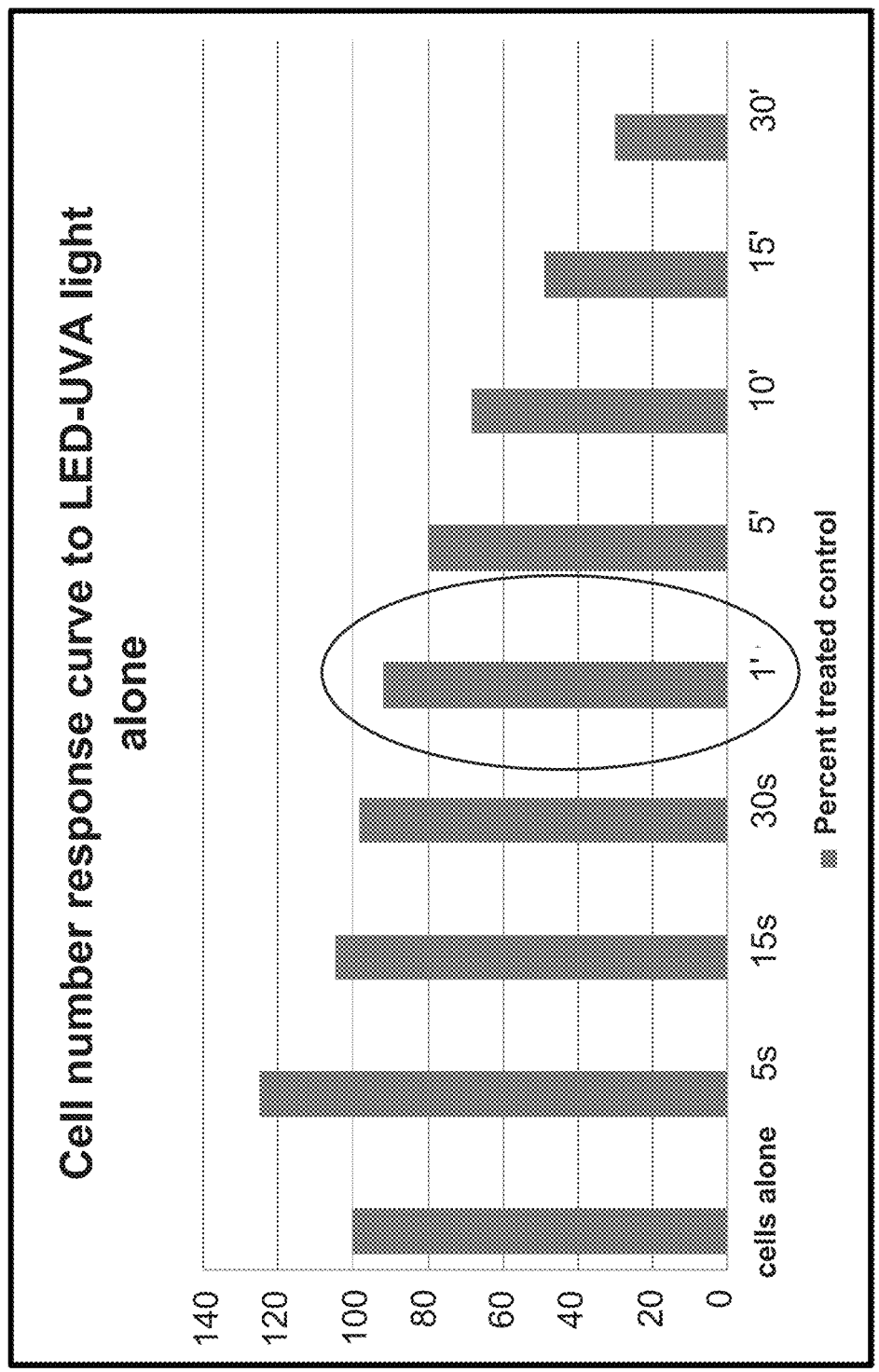
FIGS. 12-14 are charts showing the effects of UVA radiation and/or oxytetracycline on differentiated PC12 cells from test data.
Figure 13:
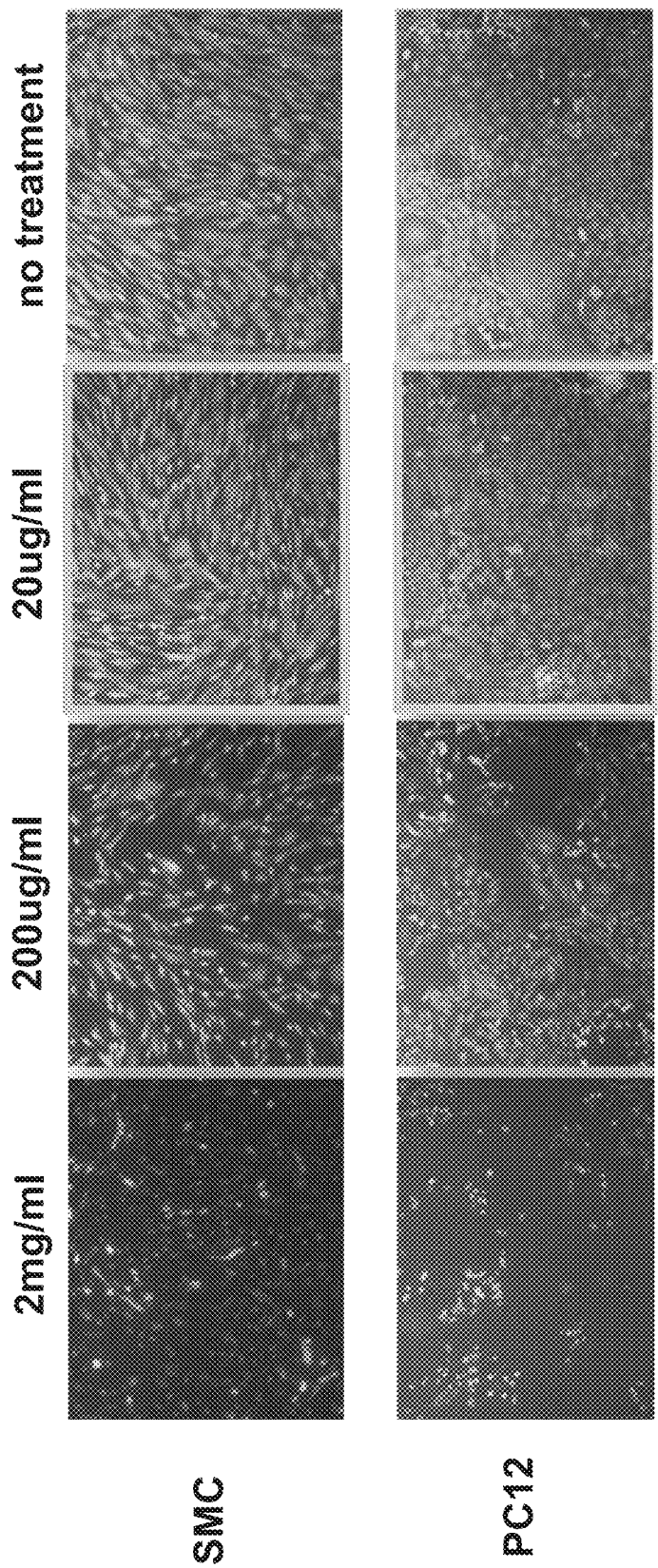

The selective disruption of neural cells using oxytetracycline was evaluated to determine whether irradiated oxytetracycline produced a lower cell count compared to control cells. PC12 cells were seeded into collagen coated 96 well plates, and a nerve growth factor (NGF) was added seven days before PC12 to induce cell differentiation. To determine an amount of UVA radiation that would have a nominal effect on cell death, the cells were exposed to titrating amounts of radiation, and then post-exposure cells were incubated for 24 hours before being washed twice, allowed to incubate for one hour, stained with Pico Green, and then counted using a Wallace plate reader. FIG. 12 is a graph showing that at a treatment time of 30-60 seconds the UVA alone started to reduce the cell count. An exposure time of 1 minute was selected for the test as being representative of an exposure where UVA would not significantly affect cell count. Another test was performed to assess the cell count of smooth muscle cells (SMC) and PC12 cells treated with oxytetracycline without irradiation. In this procedure, SMC and PC12 cells were seeded into collagen dishes, NGF was added seven days before PC12 to induce cell differentiation, both the SMC and PC12 cells were dosed with titrating amounts of tetracycline (e.g., 0 μg/ml, 20 μg/ml, 200 μg/ml, and 2 mg/ml), the oxytetracycline dosed cells were incubated for 24 hours, and then the cells were stained with Calcein AM-EtBr 1 μM for 30 minutes. FIG. 13 is a series of views showing the cell loss (dark areas) due to the oxytetracycline. Based on FIG. 13, a dosage of 20 μg/ml was selected as an amount that generally produced the same cell count in SMC and PC12 cells over a 24 hour incubation period.

Figure 14:
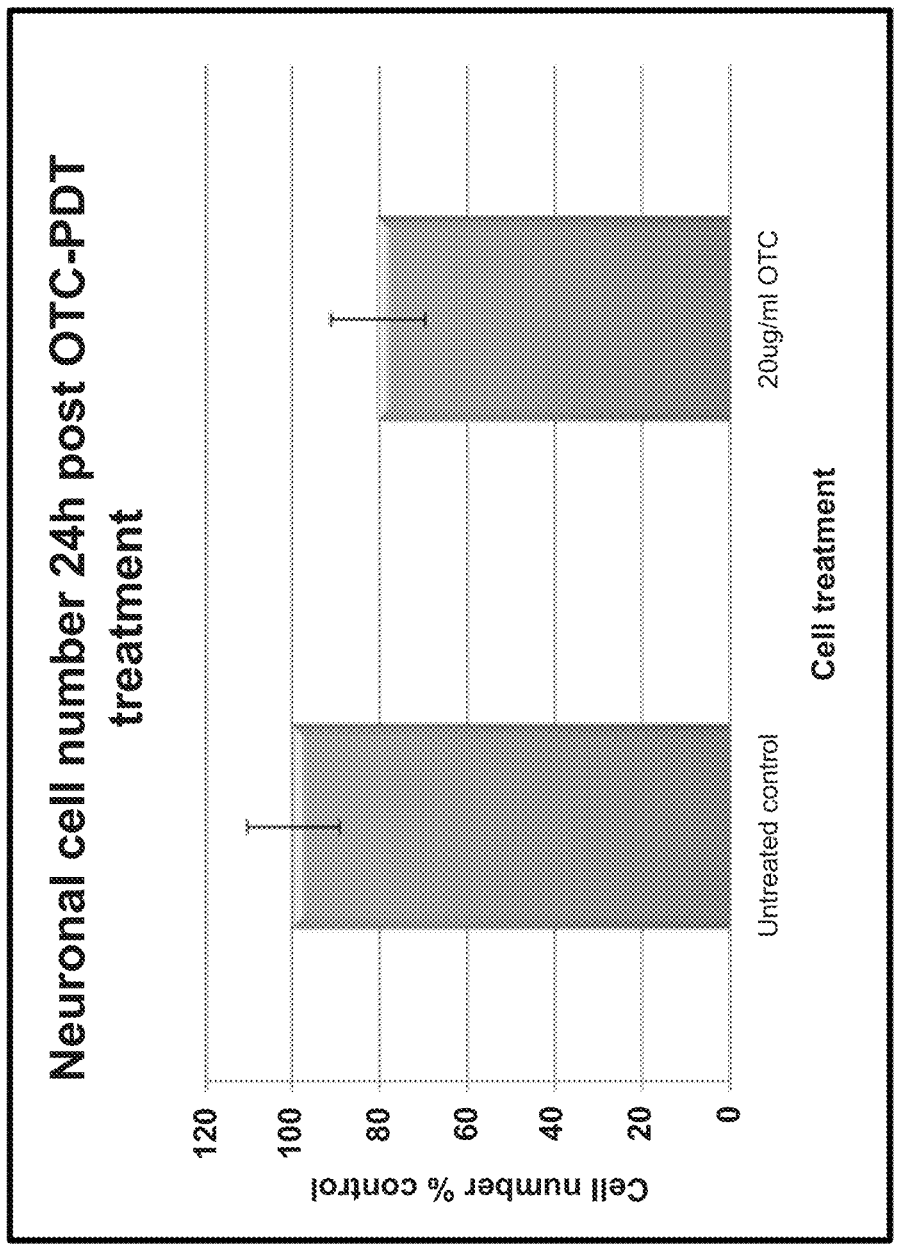

The final phase of the test included seeding PC12 cells into collagen coated 96 plates. An NGF was added seven days before PC12 cells to induce cell differentiation. The control cells and the PC12 cells were then dosed with 20 μg/ml of oxytetracycline for 24 hours. The test cells were exposed to UVA radiation at a wavelength of approximately 365 nm using an LEDMOD® Series Laser manufactured by Omicron-Laser, Germany, and an X-Cite® optical power measurement system, Lumen Dynamics Group, Inc., washed twice, stained with Pico Green, and then counted using a Wallace plate reader. FIG. 14 is a graph showing that the cells irradiated by the oxytetracycline were approximately 20% less than the cells of the carrier control group that were not irradiated. This test shows that neuronal cells exposed to UVA

EXAMPLES

Example 1

A method for therapeutic neural denervation in a human, comprising:
administering a photosensitizer to a human, wherein the photosensitizer preferentially accumulates at nerves proximate a blood vessel compared to non-neural tissue of the blood vessel; and
irradiating the photosensitizer using a radiation emitter positioned within the human, wherein the radiation has a wavelength that causes the photosensitizer to react and alter at least a portion of the nerves thereby providing a therapeutic reduction in sympathetic neural activity.

Example 2

A therapeutic neural modulation method in a human for therapeutically reducing sympathetic neural activity, comprising:
providing a photosensitizer to perivascular neural tissue associated with sympathetic neural activity, wherein the photosensitizer selectively binds to perivascular neural tissue compared to non-neural vascular tissue;
positioning a radiation emitter of treatment device in a blood vessel of the human at a target site for the perivascular neural tissue; and
emitting radiation from the radiation delivery device such that the perivascular neural tissue is irradiated by the radiation, wherein the radiation causes the photosensitizer to react and thereby disrupt the perivascular neural tissue such that neural communication along the perivascular neural tissue is at least partially inhibited.

Example 3

A method for operating a photodynamic system, comprising:
providing a photosensitizer that preferentially binds to calcium;
generating radiation at a wavelength; and
delivering the radiation to the photosensitizer.

Example 4

The method of any of examples 1-3, wherein the radiation has a wavelength of 350 nm-365 nm.

Example 5

The method of any of examples 1-3, wherein the radiation has a wavelength of 351 nm-355 nm.

Example 6

The method of any of examples 1-5, wherein the photosensitizer is administered or provided at a dosage of 0.5-1 mg/kg.

Example 7

The method of any of examples 1-5, wherein the photosensitizer is administered or provided at a dosage of 1-49 mg/kg.

Example 8

The method of any of examples 1-5, wherein the photosensitizer is administered or provided at a dosage of 50-300 mg/kg.

Example 9

The method of any of examples 1-5, wherein the photosensitizer is administered or provided at a dosage of 300-600 mg/kg.

Example 10

The method of any of examples 1-9, wherein the radiation has a dosage of 0.5-1 $J/cm^2$.

Example 11

The method of any of examples 1-9, wherein the radiation has a dosage of 5-25 $J/cm^2$.

Example 12

The method of any of examples 1-9, wherein the radiation has a dosage of 25-100 $J/cm^2$.

Example 13

The method of any of examples 1-9, wherein the radiation has a dosage of 100-500 $J/cm^2$.

Example 14

The method of any of examples 1-13, wherein the radiation is pulsed at a pulse rate of 2 ps-50 ps.

Example 15

The method of any of examples 1-14, wherein the photosensitizer is administered or provided approximately 30-180 minutes before irradiating the photosensitizer.

Example 16

The method of any of examples 1-14, wherein the photosensitizer is administered or provided approximately 3-24 hours before irradiating the photosensitizer.

Example 17

The method of any of examples 1-16, wherein the photosensitizer becomes toxic to the nerves proximate the blood vessel upon reacting with the radiation without impairing function of the non-neural tissue of the blood vessel.

Example 18

The method of any of examples 1-17, wherein the photosensitizer preferentially binds to calcium in the nerves proximate the blood vessel.

Example 19

The method of any of examples 1-18, wherein administering or providing the photosensitizer comprises injecting the photosensitizer into tissue for systemic distribution of the photosensitizer.

radiation and a dosage of oxytetracycline have a lower survival rate than the control cells.

Example 20

The method of any of examples 1-18, wherein administering or providing the photosensitizer comprises orally ingesting the photosensitizer for systemic distribution of the photosensitizer.

Example 21

The method of any of examples 1-18, wherein administering or providing the photosensitizer comprises injecting the photosensitizer proximate perivascular nerves that extend along the blood vessel.

Example 22

The method of any of examples 1-21, wherein irradiating the photosensitizer comprises inserting a catheter into the renal artery and directing the radiation through the renal artery wall to renal nerves.

Example 23

The method of any of examples 1-22, wherein irradiating the blood vessel includes emitting the radiation in a spiral pattern about an inner wall of the blood vessel.

Example 24

The method of any of examples 1-22, wherein irradiating the blood vessel includes emitting the radiation at a plurality of locations spaced apart from each other at offset circumferential positions along a length of the blood vessel.

Example 25

The method of any of examples 1-22, wherein irradiating the blood vessel includes emitting a circumferential pattern of radiation around a common plane perpendicular to the blood vessel.

Example 26

The method of any of examples 1-25, further comprising positioning the radiation emitter in a blood vessel as set forth in TABLE 1 for modulating the corresponding target nerve and thereby treating the corresponding disease/condition/etiology.

Example 27

The method of any of examples of 1-26, wherein the photosensitizer comprises oxytetracycline.

Example 28

The method of any of examples 1-26, wherein the photosensitizer comprises furocoumarins.

Example 29

The method of any of examples 1-26, wherein the photosensitizer comprises prophyrins.

Example 30

The method of any of examples 1-26, wherein the photosensitizer comprises benzoporphyrin or a derivative thereof.

Example 31

The method of any of examples 1-26, wherein the photosensitizer comprises phthaloxyanines.

Example 32

A system for performing photodynamic therapy, comprising:
a treatment device having an elongated shaft and a radiation unit at a distal portion of the elongated shaft, wherein the radiation unit has a positioning member and at least one radiation emitter, and wherein the positioning member is configured to have a low-profile delivery state for intravascular passage to a target site and a deployed state in which the positioning member is configured to contact a wall of a body lumen such that the radiation emitter is stabilized at a desired location relative to target tissue; and
a controller configured to be coupled to the treatment device, wherein the controller is adapted to cause radiation at a wavelength of 351 nm-365 nm to be delivered from the radiation unit to deliver 0.5-5 $J/cm^2$, 5-25 $J/cm^2$, 25-100 $J/cm^2$, or 100-500 $J/cm^2$ of radiation to a target.

Example 33

The system of example 32, wherein the controller has a radiation source and the radiation emitter of the radiation unit comprises an optic element configured to distributed the radiation to the target tissue, and wherein the system further comprises a light guide coupled to the controller and the optic element to transmit the radiation from the controller to the optic element.

Example 34

The system of example 32, wherein the controller has a power source and the radiation emitter of the radiation unit comprises a radiation generator coupled to the positioning member, and wherein the system further comprises an electrical lead electrically coupled to the power source and the radiation generator.

Example 35

The system of example 34, wherein the radiation generator comprises a light emitting diode.

Example 36

The system of example 34, wherein the radiation generator comprise an array of light emitting diodes.

Example 37

A device for therapeutically modulating sympathetic neural system activity, comprising:
an elongated shaft configured to pass through vascular passages of a human;
a balloon at a distal portion of the elongated shaft, the balloon having a wall configured to contact an inner wall of a blood vessel and an exterior channel through which blood can flow when inflated to a deployed state; and
a radiation element at the balloon configured to deliver radiation to perivascular nerves along the blood vessel.

Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Certain aspects of the present technology may take the form of computer-executable instructions, including routines executed by a controller or other data processor. In some embodiments, a controller or other data processor is specifically programmed, configured, and/or constructed to perform one or more of these computer-executable instructions. Furthermore, some aspects of the present technology may take the form of data (e.g., non-transitory data) stored or distributed on computer-readable media, including magnetic or optically readable and/or removable computer discs as well as media distributed electronically over networks. Accordingly, data structures and transmissions of data particular to aspects of the present technology are encompassed within the scope of the present technology. The present technology also encompasses methods of both programming computer-readable media to perform particular steps and executing the steps.

The methods disclosed herein include and encompass, in addition to methods of practicing the present technology (e.g., methods of making and using the disclosed devices and systems), methods of instructing others to practice the present technology. For example, a method in accordance with a particular embodiment includes locating a distal end portion of an elongate shaft within or otherwise proximate to a vessel or lumen of a human patient, partially decoupling a neuromodulation element from the distal end portion, expanding a support structure of the neuromodulation element radially outward relative to a central longitudinal axis of the vessel or lumen so as to move a therapeutic element carried by the support structure toward a wall of the vessel or lumen, modulating one or more nerves of the patient using the therapeutic element while the neuromodulation element is partially decoupled from the distal end portion, conveying energy toward the therapeutic element via a flexible tether extending between the distal end portion and the neuromodulation element while modulating the one or more nerves. A method in accordance with another embodiment includes instructing such a method.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A method for therapeutic neural denervation in a human patient, the method comprising:
    administering a photosensitizer to the patient, wherein
        the photosensitizer comprises oxytetracycline administered at a dosage of 0.5-600mg/kg body weight, and
        wherein the photosensitizer selectively accumulates at nerves proximate a blood vessel compared to non-neural tissue of the blood vessel;
    irradiating the photosensitizer at the nerves proximate the blood vessel via radiation from a radiation emitter positioned within the human, wherein
        the oxytetracycline is administered 0.5-24 hours before irradiating the photosensitizer, and the radiation is pulsed at of 2 ps- 50 ps to a dosage of 0.5-500 J/cm$^2$, and
    wherein the radiation has a wavelength that causes the photosensitizer to react and alter at least a portion of the nerves thereby providing a therapeutic reduction in sympathetic neural activity.

2. The method of claim 1, wherein the radiation has a wavelength of 350 nm - 365 nm.

3. The method of claim 1, wherein the radiation has a wavelength of 351 nm - 355 nm.

4. The method of claim 1, wherein the photosensitizer becomes toxic to the nerves proximate the blood vessel upon reacting with the radiation without impairing function of the non-neural tissue of the blood vessel.

5. The method of claim 1, wherein the photosensitizer selectively binds to calcium in the nerves proximate the blood vessel.

6. The method of claim 1, wherein administering the photosensitizer comprises injecting the photosensitizer into tissue for systemic distribution of the photosensitizer.

7. The method of claim 1, wherein administering the photosensitizer comprises orally ingesting the photosensitizer for systemic distribution of the photosensitizer.

8. The method of claim 1, wherein administering the photosensitizer comprises injecting the photosensitizer proximate perivascular nerves that extend along the blood vessel.

9. The method of claim 1, wherein irradiating the photosensitizer comprises inserting a catheter into the renal artery and directing the radiation through the renal artery wall to renal nerves.

10. The method of claim 1, wherein irradiating the photosensitizer includes emitting the radiation in a spiral pattern about an inner wall of the blood vessel.

11. The method of claim 1, wherein irradiating the photosensitizer includes emitting the radiation at a plurality of locations spaced apart from each other at offset circumferential positions along a length of the blood vessel.

12. The method of claim 1, wherein irradiating the photosensitizer includes emitting a circumferential pattern of radiation around a common plane perpendicular to the blood vessel.

13. A therapeutic neural modulation method in a human for therapeutically reducing sympathetic neural activity, the method comprising:
   providing a photosensitizer to perivascular neural tissue of the human associated with sympathetic neural activity, wherein
      the photosensitizer comprises oxytetracycline administered at a dosage of 0.5-600 mg/kg body weight, and
      the photosensitizer selectively binds to perivascular neural tissue compared to non-neural vascular tissue;
   positioning a radiation emitter in a blood vessel of the human at a target site for the perivascular neural tissue; and
   emitting radiation from the radiation emitter such that the perivascular neural tissue is irradiated by the radiation, wherein
      the oxytetracycline is administered 0.5-24 hours before the perivascular neural tissue is irradiated, and
      the radiation is pulsed at 2 ps-50 ps to a dosage of 0.5-500 J/cm$^2$, and
   wherein the radiation causes the photosensitizer to react and thereby disrupt the perivascular neural tissue such that neural communication along the perivascular neural tissue is at least partially inhibited.

14. The method of claim 13, wherein the radiation has a wavelength of 350 nm - 365 nm.

15. The method of claim 13, wherein the radiation has a wavelength of 351 nm - 355 nm.

16. The method of claim 13, wherein the photosensitizer becomes toxic to the perivascular nerves upon reacting with the radiation without impairing function of the non-neural tissue of the blood vessel.

17. The method of claim 13, wherein the photosensitizer selectively binds to calcium in the nerves proximate the blood vessel.

18. The method of claim 13, wherein providing the photosensitizer to the perivascular neural tissue comprises injecting the photosensitizer into tissue for systemic distribution photosensitizer.

19. The method of claim 13, wherein providing the photosensitizer to the perivascular neural tissue comprises orally ingesting the photosensitizer for systemic distribution.

20. The method of claim 13, wherein providing the photosensitizer to the perivascular neural tissue comprises injecting the photosensitizer proximate perivascular nerves that extend along the blood vessel.

21. The method of claim 13, wherein;
   positioning a radiation emitter in a blood vessel of the human comprises inserting a catheter carrying the radiation emitter into a renal artery; and
   emitting radiation from the radiation emitter comprises directing the radiation through the renal artery wall to renal nerves that extend along the renal artery.

22. The method of claim 13, wherein emitting radiation from the radiation emitter includes emitting the radiation in a spiral pattern about an inner wall of the blood vessel.

23. The method of claim 13, wherein emitting radiation from the radiation emitter includes emitting the radiation at a plurality of locations spaced apart from each other at offset circumferential positions along a length of the blood vessel.

24. The method of claim 13, wherein emitting radiation from the radiation emitter includes emitting a circumferential pattern of radiation around a common plane perpendicular to the blood vessel.

* * * * *

UNITED STATES PATENT AND TRADEMARK OFFICE
CERTIFICATE OF CORRECTION

PATENT NO.         : 8,951,296 B2
APPLICATION NO.    : 13/826604
DATED              : February 10, 2015
INVENTOR(S)        : Melder et al.

It is certified that error appears in the above-identified patent and that said Letters Patent is hereby corrected as shown below:

In the Claims

In column 20, line 36-39

"… the oxytetracycline is administered 0.5-24 hours before irradiating the photosensitizer, and the radiation is pulsed at of 2 ps- 50 ps to a dosage of 0.5-500 J/cm2, and …"

should read

-- "… the oxytetracycline is administered 0.5-24 hours before irradiating the photosensitizer, and the radiation is pulsed at 2 ps- 50 ps to a dosage of 0.5-500 J/cm2, and …" --

Signed and Sealed this
Twenty-ninth Day of December, 2015

Michelle K. Lee
*Director of the United States Patent and Trademark Office*